United States Patent [19]

Chabardes et al.

[11] 4,049,718
[45] Sept. 20, 1977

[54] SULPHONES

[75] Inventors: Pierre Chabardes, Sainte Foy les Lyon; Marc Julia, Paris; Albert Menet, La Mulatiere, all of France

[73] Assignee: Rhone-Poulenc, S.A., Paris, France

[21] Appl. No.: 548,787

[22] Filed: Feb. 10, 1975

Related U.S. Application Data

[62] Division of Ser. No. 413,246, Nov. 6, 1973.

[30] Foreign Application Priority Data

Nov. 8, 1972  France .............................. 72.39513

[51] Int. Cl.$^2$ .......................................... C07C 147/06
[52] U.S. Cl. ........................ 260/590 C; 260/666 A; 260/607 AR; 260/666 C; 260/675.5
[58] Field of Search .......................... 260/590, 607 AR

[56] References Cited

U.S. PATENT DOCUMENTS 3,865,878   2/1975   Chabardes et al. .................. 260/590

Primary Examiner—Delbert R. Phillips

Attorney, Agent, or Firm—Stevens, Davis, Miller & Mosher

[57] ABSTRACT

Sulphones of the formula:

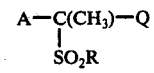

in which R is a substituted or unsubstituted alkyl, alkylaryl, aralkyl, or aryl radical, A is a radical containing one or more isoprene units which is saturated, unsaturated, or of the conjugated or unconjugated polyene type, which is unsubstituted or substituted by one or more functional groups, halogen atoms or alkyl groups, and which may be cyclic when the number of isoprene units is at least 2, and Q is hydrogen or a cyclic or acyclic hydrocarbon radical which is saturated, unsaturated, or of the conjugated or unconjugated polyene type, and which is unsubstituted or substituted by one or more functional groups, halogen atoms or alkyl groups are useful intermediates in the production of terpene compounds such as $\beta$-carotene and canthaxanthine.

6 Claims, No Drawings

SULPHONES

This is a division of application Ser. No. 413,246, filed 11/6/73, now pending.

The present invention relates to sulphones and their use in synthesis.

The sulphones of the invention have the formula:

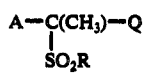
(I)

in which R is a substituted or unsubstituted alkyl, alkylaryl, aralkyl or aryl radical, A is a radical containing one or more isoprene units which is saturated, unsaturated or of the conjugated or unconjugated polyene type, which is unsubstituted or substituted by one or more functional groups, halogen atoms, or alkyl groups, and which may be cyclic when the number of isoprene units is at least 2, and Q is hydrogen or a cyclic or acyclic hydrocarbon radical which is saturated, unsaturated, or of the conjugated or unconjugated polyene type and which is unsubstituted or substituted by one or more functional groups halogen atoms or alkl groups.

The radical A can, for example, carry the following functional groups: an alcohol group, which may be etherified or esterified with an inorganic or organic acid, a free or protected aldehyde group, an acid group or a derivative thereof such as an acid chloride, ester, amide or nitrile, or a group —SR' or —SO$_2$R' in which R is an alkyl, alkylaryl, aryl or aralkyl radical. When A is cyclic, it may be substituted by, for example, =O or —OH, which may be free of protected.

Q may be substituted by, for example, methyl groups. Q can also contain a ring to which alkyl groups and/or functional groups such as O= or —OH are optionally attached, the latter being free or protected. Q can also be halogenated and/or carry the same functional groups as those mentioned above for A.

A preferred class of compounds of formula I are those in which A is methyl or a hydrocarbon radical having the carbon skeleton

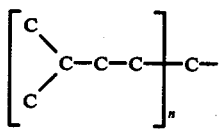

which may be cyclic and which contains an odd number of hydrogen atoms from $8n + 1$ to $10n + 3$ or such a radical substituted by an oxo radical. Q is hydrogen, a radical within the aforesaid definition of A, or a radical of formula:

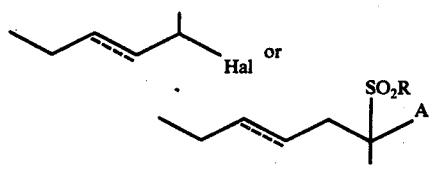

where Hal is halogen, A is as hereinbefore defined, R is as hereinbefore defined and the indicated bonds are single or double, and $n$ is an integer from 1 to 3. Particular preferred radicals which may be represented by A are those of formulae:

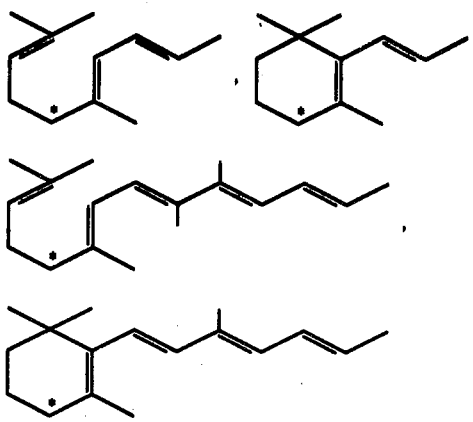

or such a radical substituted on the carbon atom marked by an asterisk by oxo, and preferred radicals which may be represented by Q are hydrogen, or a radical of formula:

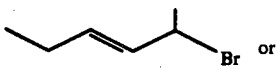 or

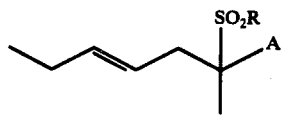

where A is as hereinbefore defined.

The compounds of the formula (I) in which Q represents a hydrogen atom, which consequently have the formula:

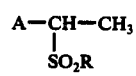
(II)

are hereafter called secondary sulphones in order to indicate that the sulphone group is carried by a secondary carbon, and the compounds of the formula I in which Q represents a radical other than hydrogen are hereafter called tertiary sulphones.

The secondary sulphones can be prepared by reacting an alcohol of the formula A—CHOH—CH$_3$ with an alkali metal sulphinate of formula RSO$_2$M in the presence of an inorganic or organic acid. Denoting the latter by HAc, the reaction can be represented by the following equation:

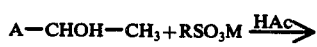

M being an alkali metal. This reaction can also be applied to an isomer of the secondary alcohol ACHOHCH$_3$ which is capable of changing into the latter during the reaction.

The reaction can be carried out in a solvent such as a hydrocarbon, an alcohol or an ether. The temperature can vary from −20° to +100° C, and in the majority of cases it is +10° to +40° C.

The compounds of the formula (II) can also be prepared by reaction of a halide of the formula A—CHX—CH$_3$ in which A is as defined above and X represents a halogen atom, with an alkali metal sulphinate of formula RSO$_2$M. The reaction can be represented by the following equation:

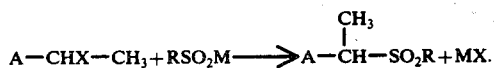

It is preferably carried out in a solvent or a mixture of solvents such as a hydrocarbon, e.g. hexane, benzene or toluene, an alcohol such as methanol or ethanol, a linear or cyclic ether such as diethyl ether, dioxan or tetrahydrofuran, or dimethylsulphoxide, dimethylformamide, dimethylacetamide or hexamethyl-phosphoramide. The reaction takes place easily under mild conditions and isolation of the desired sulphone does not present any difficulty, because the alkali metal halide formed during the reaction can be removed by simply washing the reaction mixture with water.

Suitable secondary alcohols which may be used to prepare the sulphones of formula (I) include secondary alcohols produced by selective hydrogenation of commercially known ketones such as methyl-heptenone, ionones, irones and pseudo-iononeses.

The halides maybe prepared by halogenation of the secondary alcohols A—CHOH—CH$_3$, or their isomers, with a phosphorus trihalide, thionyl chloride or phosgene, by the usual methods for carrying out this kind of reaction.

Tertiary sulphones of the formula (I) in which Q represents a radical as defined above can be prepared by reaction of a secondary sulphone of the formula (II) with a halide of the formula Q′X in which Q′ has the same definition as Q but is not hydrogen atom and X is a halogen atom, in the presence of a basic agent. This reaction can be represented as follows:

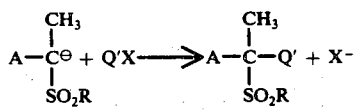

where X is chlorine or bromine.

The basic agent must possess sufficient basicity to anionise the secondary sulphone and to make it possible to attach the radical Q′ to it. Inorganic or organic compounds such as alkali metal hydroxides, alcoholates, hydrides or amides can be used; organometallic compounds such as organo-zinc compounds, organo-lithium compounds and organo-magnesium compounds are also suitable. These anionisation agents can be used alone or together with another basic agent intended to neutralise the hydrogen halide formed. Where the anionising agent is used along, the quantity employed must be sufficient to achieve this neutralisation. The quantity also depends on the method of carrying out the reaction and of the reactivity of the reaction products with respect to this basic agent. For these reasons, it can be advantageous to employ a smaller quantity of anionising agent in the reaction and to add another basic agent to which the reaction products are less sensitive and which neutralises the hydrogen halide formed.

The reaction is carried out at a temperature from −100° C to +150° C, depending on the nature of the products employed and produced.

In order that the reaction shall take place satisfactorily, it is advantageous to carry it out in an organic solvent which can be a hydrocarbon such as hexane, benzene or toluene, a protic solvent, e.g. methanol, ethanol or ethylene glycol, or a linear or cyclic ether of a mono-alcohol or a diol such as diethyl ether, dioxan or tetrahydrofuran. Other solvents such as, for example, dimethylformamide, dimethylacetamide, dimethylsulphoxide, N-methyl-pyrrolidone and hexamethylphosphotriamide can also be used.

If a secondary sulphone is condensed with a compound carrying two halogen atoms on two different carbon atoms, a tertiary disulphone is obtained. For example, when the dihalide is 1,4-dichloro-2-butene or 1,4-dibromo-2-butene, the reaction proceeds, e.g. as follows:

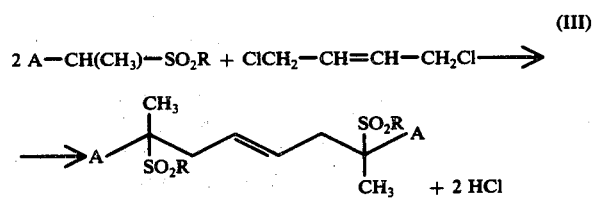

and the disulphone product can be particularly valuable for the synthesis of carotenoids.

Tertiary sulphones can be subjected to a reducing desulphonation treatment and compounds of the formula A—CH(CH$_3$)Q′ are then obtained. They can also be treated with an inorganic or organic basic agent such as, for example, an alkali metal hydroxide, carbonate or alcoholate; the products then obtained possess an ethylenic double bond and have the formula A—C(CH$_3$)=Q′. Basic desulphonation of the disulphones represented in equation (III) leads to compounds of the formula

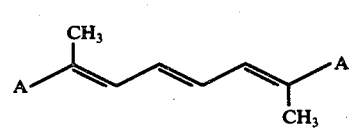

which have the tail-to-tail isoprene chain linkage characteristic of the carotenoids.

Depending on the method of desulphonation chosen, it is possible to prepare terpenes, acyclic or cyclic products such as myrcene, geraniol, citronnellol, citral, geranic acid and its esters, farnesal, farnesol and its esters, farnesic acid and its derivatives, axerophthene and its lower or high isoprenologues and the functional derivatives of the same series, particularly retinal and its acetals, vitamin A (retinol), its ethers and its esters, vitamin A-acid, its esters and its nitrile, other functional derivatives of retinene such as 4-oxo-retinal, apocarotenals and the corresponding alcohols as well as their ethers and their esters, apocarotenic acids and their derivatives. Carotenoid compounds containing 40 carbon atoms or more can also be prepared: there may be mentioned, inter alia, various carotenes such as β-carotene and γ-carotene, lycopene, astacene, canthaxanthine, zeaxanthine, isozeaxanthine and more generally xanthophyllic compounds corresponding to these various carotenes. Such methods of synthesis employing sulphones of formula (I) can also be used to prepare compounds, the molecule of which contains a saturated or unsaturated polyisoprene chain such as vitamin E or vitamins $K_1$ and $K_2$.

The desulphonation can be carried out on the sulphone isolated from the reaction mixture, or it can be carried out in this mixture. Whichever method is chosen, an alkali metal sulphinate or a sulphinic acid is liberated and can be re-used in the preparation of the starting sulphone, so that the synthesis of polyisoprene compounds, using these sulphones as intermediates, consumes practically no alkali metal sulphinate.

The following Examples illustrate the preparation of sulphones according to the invention and their use in organic synthesis.

EXAMPLE 1

26 g of 90% pure 2,6,6-trimethyl-8-(cyclohex-1-enyl)-6-methyl-octa-3,5,7-trien-2-ol, 31.8 g of sodium phenylsulphinate and 440 cm³ of acetic acid are introduced into a 1 liter flask. The mixture is stirred for 16 hours at ambient temperature and the excess acetic acid is then evaporated under the vacuum provided by a vane pump. The paste-like residue obtained is taken up in water and then extracted with 4 times 125 cm³ of diethyl ether. The combined ether layers are washed first with water and then with 200 cm³ of a 10% aqueous sodium bicarbonate solution, and dried over magnesium sulphate. On evaporation of the ether, 33 g of a paste-like product are obtained containing 90% of a product which has an absorption maximum at 340 nm ($E_{1\,cm}^{1\%}$ = 732) in ethanol in UV spectrography, and which corresponds to the formula

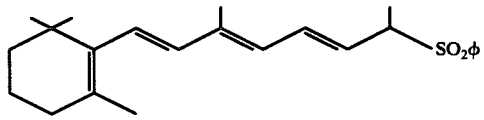

as measured by nuclear magnetic resonance.
Degree of conversion 100%. Yield 87%.

EXAMPLE 2

Following the procedure of Example 1, 25.8 g. of β-ionol are reacted with 41 g of sodium phenylsulphinate in 450 cm³ of acetic acid for 16 hours. The acetic acid is then removed and the concentrated reaction mixture is taken up in 500 cm³ of diethyl ether and 500 cm³ of distilled water. The aqueous layer is separated and extracted with twice 250 cm³ of diethyl ether. From the combined ether layers, treated as in Example 1, 33 g of a viscous, slightly hellow-coloured liquid are isolated, containing 26.4 g of the compound of the formula

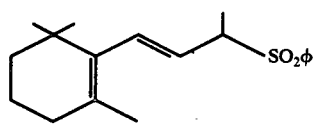

On recrystallisation from diisopropyl ether, this product is a while crystalline product, m.p. 50° C.
Yield 62.4%.

EXAMPLE 3

A solution of 3.88 g of pseudo-ionol in 40 cm³ of acetic acid is added to a solution of 7.12 g of sodium p-toluenesulphinate in 40 cm³ of acetic acid. The reaction is allowed to continue with stirring and at ambient temperature, for 16 hours. The acetic acid is then evaporated and the residue taken up in a mixture of 50 cm³ of water and 25 cm³ of diethyl ether.

After separation, washing the aqueous layer with twice 20 cm³ of diethyl ether, and treating the combined ether layers as in Example 1, a viscous yellow liquid is obtained containing a product of the formula

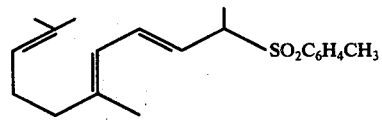

measured by UV spectrography and nuclear magnetic resonance.
Degree of conversion 100%. Yield 93.5%.

EXAMPLE 4

2.34 g of 8-(2,6,6-trimethyl-cyclohex-1-enyl)-6-methyl-octa-3,5,7-trien-2-ol is reacted with 3.88 g of sodium p-methoxyphenylsulphinate in 45 cm³ of acetic acid with stirring, at 25° C. After removing the acetic acid, the residue is taken up in a mixture of 100 cm³ of water and 100 cm³ of diethyl ether. The mixture is separated, the aqueous layer is extracted with twice 25 cm³ of diethyl ether, and the combined ether layers are worked up as in the preceding Examples. 2.9 g of a pure product, identified and measured by UV spectrography and nuclear magnetic resonance, which has the formula

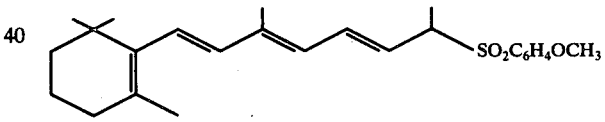

are thus obtained.

The sodium p-methoxyphenylsulphinate used was prepared from p-methoxyphenylsulphonyl chloride by the process described in Acta chemical Scandinavica, 17, page 380, 1963.

EXAMPLE 5

4.86 g of sodium methoxide in 120 cm³ of tetrahydrofuran are introduced into a 500 cm³ flask equipped with a dropping funnel and then, after the mixture has been cooled to −10° C, 13.32 g of 8-(2,6,6-trimethyl-cyclohex-1-enyl)-6-methyl-2-phenylsulphonyl-octa-3,5,7-triene (prepared as in Example 1) dissolved in 70 cm³ of tetrahydrofuran are added. A solution of 4.92 g of 1,4-dibromo-2-butene in 30 cm³ of tetrahydrofuran is then run in and reaction is allowed to take place for 2 hours at −10° C and then for 1 hour at ambient temperature. After having removed two-thirds of the solvent under the vacuum provided by a vane pump, the reaction mixture is poured into a mixture of 400 cm³ of water and 200 cm³ of diethyl ether. The mixture is separated, and the aqueous layer is extracted with 4 times 50 cm³ of diethyl ether. Treatment of the combined ether layers (washing with water, drying and concentration) gives 16.22 g of a crude oil containing 87% of a product which is identified by UV spectrography and nuclear magnetic resonance, as having the formula

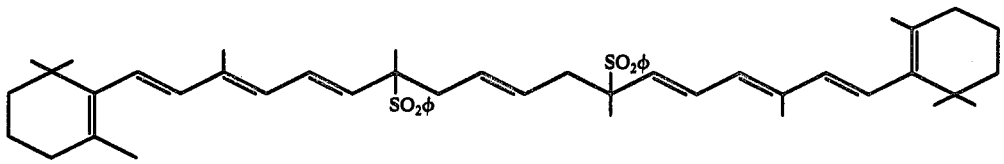

The degree of conversion is 100% and the yield is 90%.

When purified by recrystallisation from diisopropyl ether, this product has a melting point 140° – 145° C; it has an UV absorption maximum at 308 nm ($E_{1\,cm}^{1\%}$ = 780) in solution in ethanol.

1,4-Dibromo-2-butene was prepared by the process described in J. Chem. Soc. page 241, 1949, by slowly adding bromine dissolved in carbon tetrachloride to butadiene dissolved in the same solvent, the temperature being kept at −20° C.

EXAMPLE 6

Preparation of β-carotene

A mixture of 0.587 g of the sulphone prepared as in Example 5, 10 cm³ of hexane and 336 mg of potassium t-butylate is heated to 60° C. for 40 minutes and the mixture is then allowed to cool. The reaction mixture is poured into 200 cm³ of a 50/50 mixture of chloroform and water.

The organic layer is decanted, washed with water until neutral, dried and then concentrated. 0.465 g of crude β-carotene, which has an UV absorption maximum at 454 nm ($E_{1\,cm}^{1\%}$ = 1250), is thus isolated.

Degree of conversion 100%. Yield 87%.

EXAMPLE 7

3 g of the disulphone prepared in Example 5 are dissolved in 131 cm³ of chloroform, and 5 g of sodium periodate dissolved in 32.5 cm³ of water and 11 cm³ of ethyl alcohol, followed by 12.7 cm³ of 1% iodine in chloroform, are added. Reaction is allowed to take place to ambient temperature (24° C) for 65 hours and the reaction mixture is poured into a mixture of 100 cm³ of water and 40 cm³ of chloroform. The organic layer is separated, neutralised with an aqu eous solution of sodium bicarbonate, washed with water until neutral, dried over magnesium sulphate and concentrated. A solid brown product, in which a compound of the formula

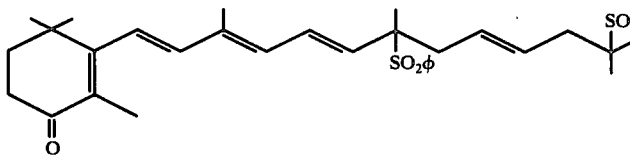

is identified, is this obtained.

Its shows two characteristic UV-absorption bands (in ethanol) at 303 nm ($E_{1\,cm}^{1\%}$ = 378) and 258 nm ($E_{1\,cm}^{1\%}$ = 388).

Degree of conversion 100%. Yield 91%.

EXAMPLE 8

Preparation of canthaxanthine 0.424 g of the disulphone prepared in Example 7 is added to 0.448 mg of potassium t-butylate in 20 cm³ of hexane and 10 cm³ of dimethylsulphoxide. The temperature is raised to 50° C and reaction is allowed to take place for 2 hours, with stirring. After cooling, the reaction mixture is poured into a mixture of 80 cm³ of water and 30 cm³ of chloroform. The aqueous layer is decanted and extracted with chloroform. The combined chloroform layers are treated as described in Example 7 and 0.500 g of product, in which canthaxanthine is identified by UV spectrography, is thus isolated.

EXAMPLE 9

8.25 g of sodium periodate, dissolved in 52.5 cm³ of water and 1.7 cm³ of ethyl alcohol, followed by 21 cm³ of 1% iodine in chloroform, are added to a solution of 4.5 g of the sulphone prepared in Example 1 in 210 cm³ of chloroform. Reaction is allowed to take place for 42 hours at ambient temperature (24° C) and the mixture is then poured into 200 cm³ of water and 100 cm³ of chloroform. The mixture is seperated and the chloroform layer is neutralised with an aqueous solution of sodium bicarbonate and washed with water. The aqueous layer is extracted 3 times with 50 cm³ of chloroform. The combined chloroform layers are dried over magnesium sulphate, filtered and concentrated, and 5.2 g of a viscous oil in which a product of the formula

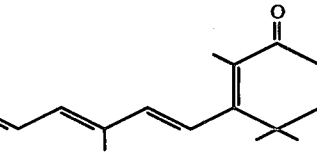

is identified and measured by nuclear magnetic resonance, are isolated.

Degree of conversion 100%. Yield 82%.

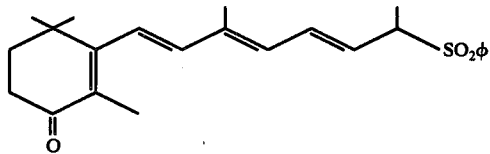

EXAMPLE 10

3.2 g of the sulphone prepared in Example 2 and 10 cm³ of tetrahydrofuran are introduced, under a nitrogen atmosphere, into a flask equipped with a reflux condenser and a dropping funnel. When dissolution is complete, the mixture is cooled to −40° C and 3.66 g of potassium t-butylate in 5 cm³ of tetrahydrofuran are then added. The mixture becomes red and is cooled to −50° C. 4.6 g of 1.4-dibromo-2-pentene dissolved in 5 cm³ of tetrahydrofuran are then added. The addition lasts for 45 minutes and is carried out with stirring. After 5 hours, the reaction mixture is poured into a mixture of 25 cm³ of iced water and 25 cm³ of diethyl ether. The mixture is separated and the aqueous layer is extracted with twice 20 cm³ of diethyl ether. The ether layers are combined, washed with water, dried, filtered and concentrated. 7.3 g of a dark orange viscous product are thus obtained, in which 4.3 g of a compound of the formula

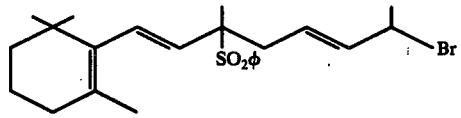

are identified and measured by nuclear magnetic resonance.

Degree of conversion 100%. Yield 94.5%.

We claim:

1. A sulphone of the formula:

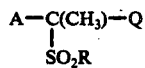

in which R is substituted or unsubstituted aryl, A is

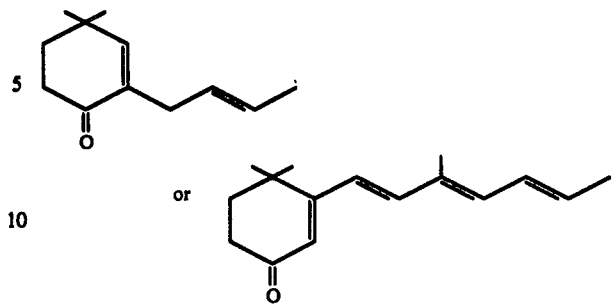

and Q is hydrogen or a radical of formula:

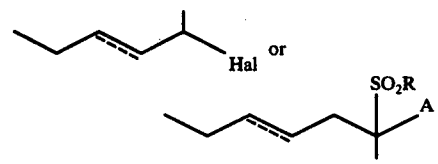

where Hal is halogen and R and A are as hereinbefore defined.

2. A sulphone according to claim 1 in which R is phenyl, tolyl, or methoxyphenyl.

3. A compound according to claim 1 which is a 8-(2,6,6-trimethyl-4-oxo-cyclohex-1-enyl)-6-methyl-2-arylsulphonyl-octa-3,5,7-triene.

4. A compound according to claim 1 which is a 13,13′-diarylsulphonyl-canthaxanthine.

5. A compound as claimed in claim 3, in which aryl is phenyl, p-tolyl, or p-methoxyphenyl.

6. A compound as claimed in claim 4, in which aryl is phenyl, p-tolyl, or p-methoxyphenyl.

* * * * *